US012702434B2

(12) United States Patent
Shiota et al.

(10) Patent No.: US 12,702,434 B2
(45) **Date of Patent: *Aug. 11, 2026**

(54) ENDOSCOPIC TREATMENT DEVICE

(71) Applicant: OLYMPUS MEDICAL SYSTEMS CORP., Hachioji (JP)

(72) Inventors: Yusuke Shiota, Machida (JP); Chika Miyajima, Hachioji (JP); Hiromasa Kato, Tokyo (JP); Kotaro Yamada, Tachikawa (JP); Tomohiro Tsuji, Hino (JP)

(73) Assignee: OLYMPUS MEDICAL SYSTEMS CORP., Tokyo (JP)

( * ) Notice: Subject to any disclaimer, the term of this patent is extended or adjusted under 35 U.S.C. 154(b) by 162 days.

This patent is subject to a terminal disclaimer.

(21) Appl. No.: 18/824,212

(22) Filed: Sep. 4, 2024

(65) Prior Publication Data

US 2024/0423657 A1 Dec. 26, 2024

Related U.S. Application Data

(63) Continuation of application No. 17/586,336, filed on Jan. 27, 2022, now Pat. No. 12,108,962.

(Continued)

(51) Int. Cl.
*A61B 17/29* (2006.01)
*A61B 17/00* (2006.01)
(Continued)

(52) U.S. Cl.
CPC .............. *A61B 17/29* (2013.01); *A61B 18/14* (2013.01); *A61B 2017/00269* (2013.01);
(Continued)

(58) Field of Classification Search
CPC .......... A61B 2017/320084; A61B 17/320068; A61B 17/320092; A61B 2217/007; A61B 2218/001–002
See application file for complete search history.

(56) References Cited

U.S. PATENT DOCUMENTS

| | | | | |
|---|---|---|---|---|
| 12,035,960 | B2 | 7/2024 | Tang et al. | |
| 2018/0325541 | A1* | 11/2018 | Kuriki ................ | A61B 18/1445 |
| 2021/0330977 | A1 | 10/2021 | Sinha | |

FOREIGN PATENT DOCUMENTS

| | | | |
|---|---|---|---|
| CN | 205359621 | U | 7/2016 |
| CN | 209529285 | U | 10/2019 |
| JP | 2013-111308 | A | 6/2013 |

OTHER PUBLICATIONS

May 21, 2025 Office Action issued in U.S. Appl. No. 17/586,390.

(Continued)

*Primary Examiner* — Brooke Labranche
*Assistant Examiner* — Rachael L Geiger
(74) *Attorney, Agent, or Firm* — Oliff PLC

(57) ABSTRACT

An endoscopic treatment device includes a sheath formed from a resin; a flow-passage formation member attached to a distal end portion of the sheath to be rotatable around a longitudinal axis of the sheath; a pair of forceps pieces supported by the flow-passage formation member such that the pair of forceps pieces are able to be opened and closed; a link mechanism connected to the pair of forceps pieces and configured to open and close the pair of forceps pieces; an operation wire extending along the longitudinal axis of the sheath; and a connection member configured to connect a proximal end arm of the link mechanism and the operation wire.

21 Claims, 11 Drawing Sheets

Related U.S. Application Data

(60) Provisional application No. 63/143,141, filed on Jan. 29, 2021.

(51) Int. Cl.
*A61B 17/32* (2006.01)
*A61B 18/00* (2006.01)
*A61B 18/12* (2006.01)
*A61B 18/14* (2006.01)

(52) U.S. Cl.
CPC ................ *A61B 2017/0034* (2013.01); *A61B 2017/2939* (2013.01); *A61B 2017/2948* (2013.01); *A61B 2017/320084* (2013.01); *A61B 2018/00488* (2013.01); *A61B 2018/00494* (2013.01); *A61B 2018/00982* (2013.01); *A61B 2018/1253* (2013.01); *A61B 2018/1425* (2013.01); *A61B 2217/007* (2013.01); *A61B 2218/002* (2013.01)

(56) References Cited

OTHER PUBLICATIONS

Mar. 26, 2024 Office Action issued in U.S. Appl. No. 17/586,336.
Jun. 27, 2024 Notice of Allowance issued in U.S. Appl. No. 17/586,336.
Dec. 3, 2025 Office Action issued in U.S. Appl. No. 17/586,390.

* cited by examiner 51
52C
4C
53C
51
5C
54C
6
15
1b
1a
100C
1c

FIG. 3

ENDOSCOPIC TREATMENT DEVICE

CROSS-REFERENCE TO RELATED APPLICATIONS

This is a Continuation of application Ser. No. 17/586,336 filed Jan. 27, 2022, which claims the benefit of U.S. Provisional Application No. 63/143,141, filed Jan. 29, 2021. The disclosure of the prior applications is hereby incorporated by reference herein in its entirety.

TECHNICAL FIELD

The present disclosure relates to an endoscopic treatment device.

BACKGROUND

Conventionally, during an endoscopic treatment such as the Endoscopic Submucosal Dissection (ESD) or the like, the endoscopic treatment device for dissection and peeling procedures such as the high-frequency knife and the like, the endoscopic treatment device for local injection procedures, and the endoscopic treatment device for hemostasis procedures are used.

The endoscopic treatment devices can be configured to be capable of performing several procedures among the dissection and the peeling procedures, the local injection procedures, and the hemostasis procedures. For example, the endoscopic high-frequency treatment device can be capable of performing the dissection procedures, the peeling procedures, and the hemostasis procedures. Or it can be capable of performing the dissection procedures, the peeling procedures, and the local injection procedures.

SUMMARY

According to an aspect of the present disclosure, an endoscopic treatment device includes a sheath formed from a resin; a flow-passage formation member attached to a distal end portion of the sheath to be rotatable around a longitudinal axis of the sheath; a pair of forceps pieces supported by the flow-passage formation member to be able to open and close; a link mechanism connected to the pair of forceps pieces and configured to open and close the pair of forceps pieces; an operation wire extending along the longitudinal axis of the sheath; and a connection member configured to connect a proximal end arm of the link mechanism and the operation wire, wherein the flow-passage formation member includes a first liquid supply hole through which the proximal end arm of the link mechanism is inserted; and a notch portion configured to form a second liquid supply hole as a gap between a distal end cover of the sheath and the notch portion, when the pair of forceps pieces are closed, part of the link mechanism is configured to block the first liquid supply hole, and when the pair of forceps pieces are open, part of the connection member is configured to block the first liquid supply hole.

BRIEF DESCRIPTION OF THE DRAWINGS

FIG. 3 is a cross-sectional view showing a distal end of the treatment device when the forceps are in a closed state.

DESCRIPTION OF EMBODIMENTS

Figure 1:
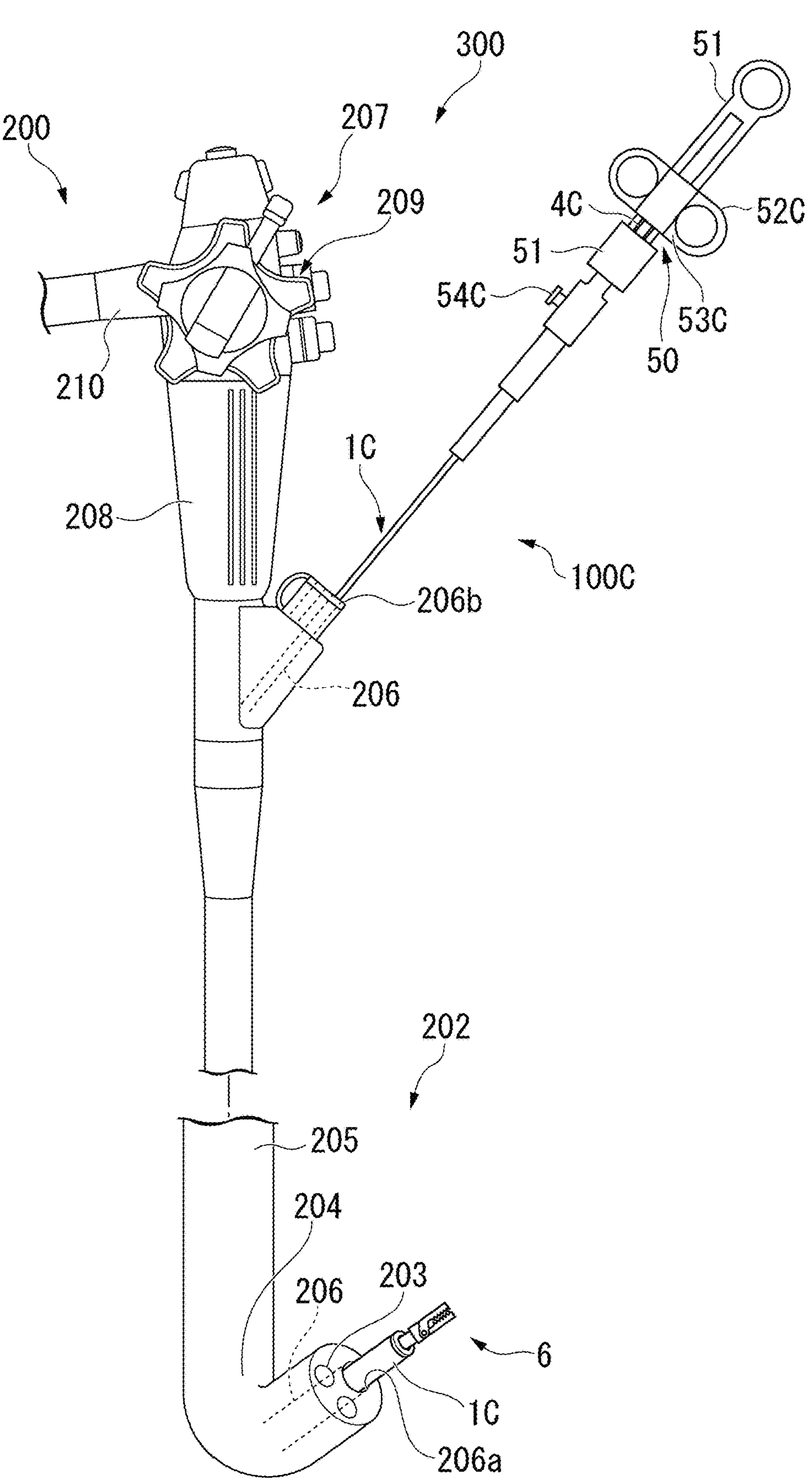
FIG. 1 is an overall view showing an endoscopic treatment system according to an exemplary embodiment.

An endoscopic treatment system 300 according to an exemplary embodiment of the present disclosure will be described by referring to FIG. 1 to FIG. 14. FIG. 1 is an overall view of the endoscopic treatment system 300 according to the present embodiment.

[Endoscopic Treatment System 300]

As shown in FIG. 1, the endoscopic treatment system 300 includes an endoscope 200 and a treatment device 100C. The treatment device 100C is inserted into the endoscope 200 to be used.

[Endoscope 200]

The endoscope 200 is a conventional flexible endoscope, and includes an insertion portion 202 being inserted into the body from a distal end, and an operation portion 207 attached to a proximal end of the insertion portion 202.

The insertion portion 202 includes an imaging portion 203, a bending portion 204, and a flexible portion 205. The imaging portion 203, the bending portion 204, and the flexible portion 205 are disposed from the distal end of the insertion portion 202 in this sequence. Inside the insertion portion 202, a channel 206 for inserting the treatment device 100C is provided. A distal end opening portion 206*a* of the channel 206 is provided at the distal end of the insertion portion 202.

The imaging portion 203 includes, for example, the imaging element such as CCD or CMOS, and is configured to be able to image the site of the treatment target. The imaging portion 203 is able to image the rod 2 of the treatment device 100C in a state in which the treatment device 100C protrudes from the distal end opening portion 206*a* of the channel 206.

The bending portion 204 is bent according to operations by an operator to the operation portion 207. The flexible portion 205 is a tubular portion having flexibility.

The operation portion 207 is connected to the flexible portion 205. The operation portion 207 includes a grip 208, an input portion 209, a proximal end opening portion 206*b* of the channel 206, and a universal cord 210. The grip 208 is a portion for the operator to grasp. The input portion 209 receives the operation input for the bending operations of the bending portion 204. The universal cord 210 is configured to output the image captured by the imaging portion 203 to the external device. The universal cord 210 is connected to a display device such as an LCD display or the like via an image processing device that includes a processor and the like.

[Treatment Device 100C]

Figure 2:
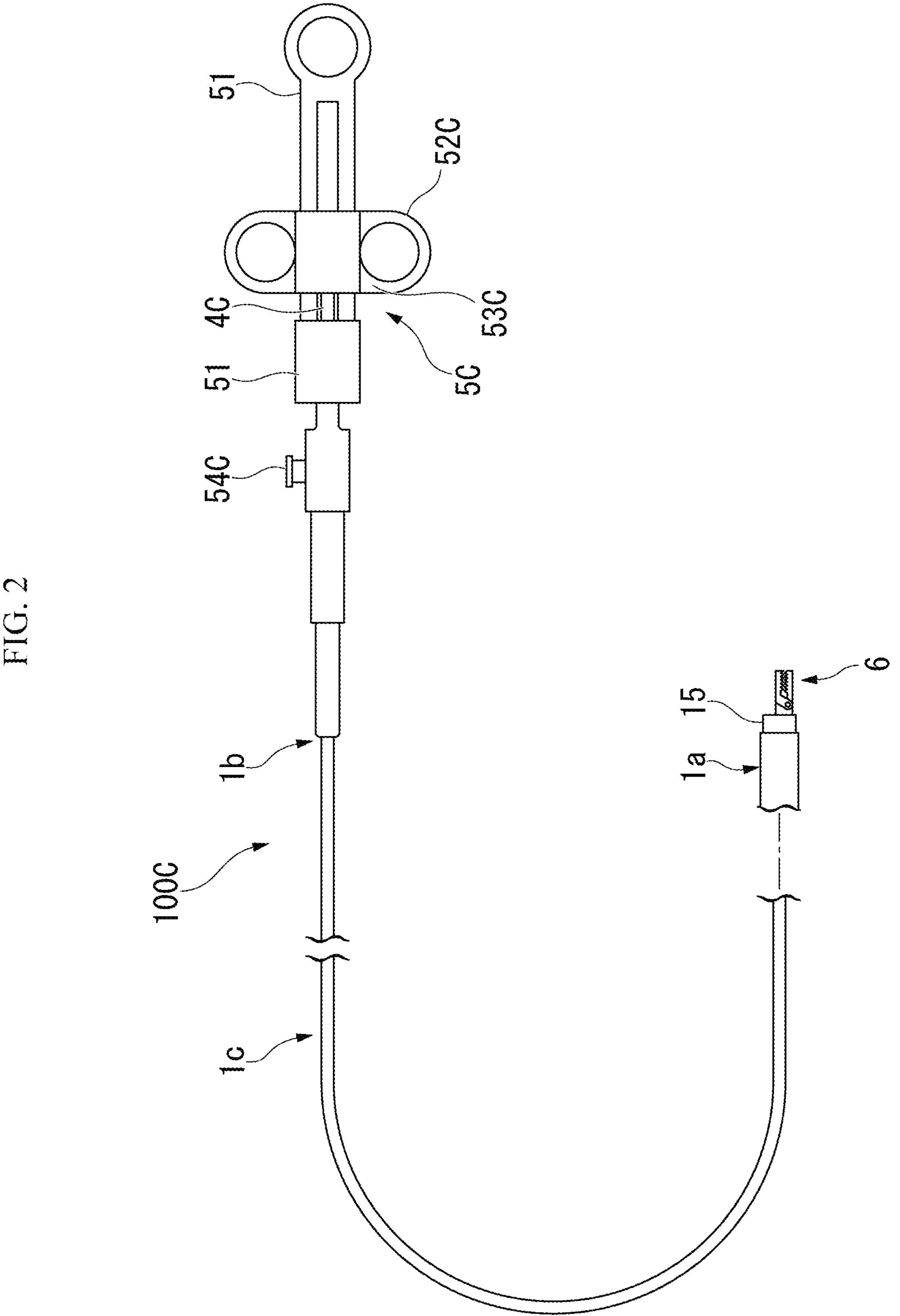
FIG. 2 is an overall view showing a treatment device of the endoscopic treatment system.

FIG. 2 is an overall view of the treatment device 100C.

The treatment device (endoscopic treatment device) 100C includes a sheath 1C, a forceps 6, a support member 7, a connection member 9, an operation wire 4C, and an operation portion 5C. In the following description, along a longitudinal direction A of the treatment device 100C, the side being inserted into the body of the patient is referred to as the "distal end side A1", and the side of the operation portion 5C is referred to as the "proximal end side A2".

The sheath 1C having flexibility and insulation properties is an elongated member extending from a distal end 1*a* to a proximal end 1*b* and the sheath 1C is made from a resin material. The sheath 1C has an outer diameter so as to be insertable into the channel 206 of the endoscope 200, and is advanceable and retractable in the channel 206.

Figure 3:
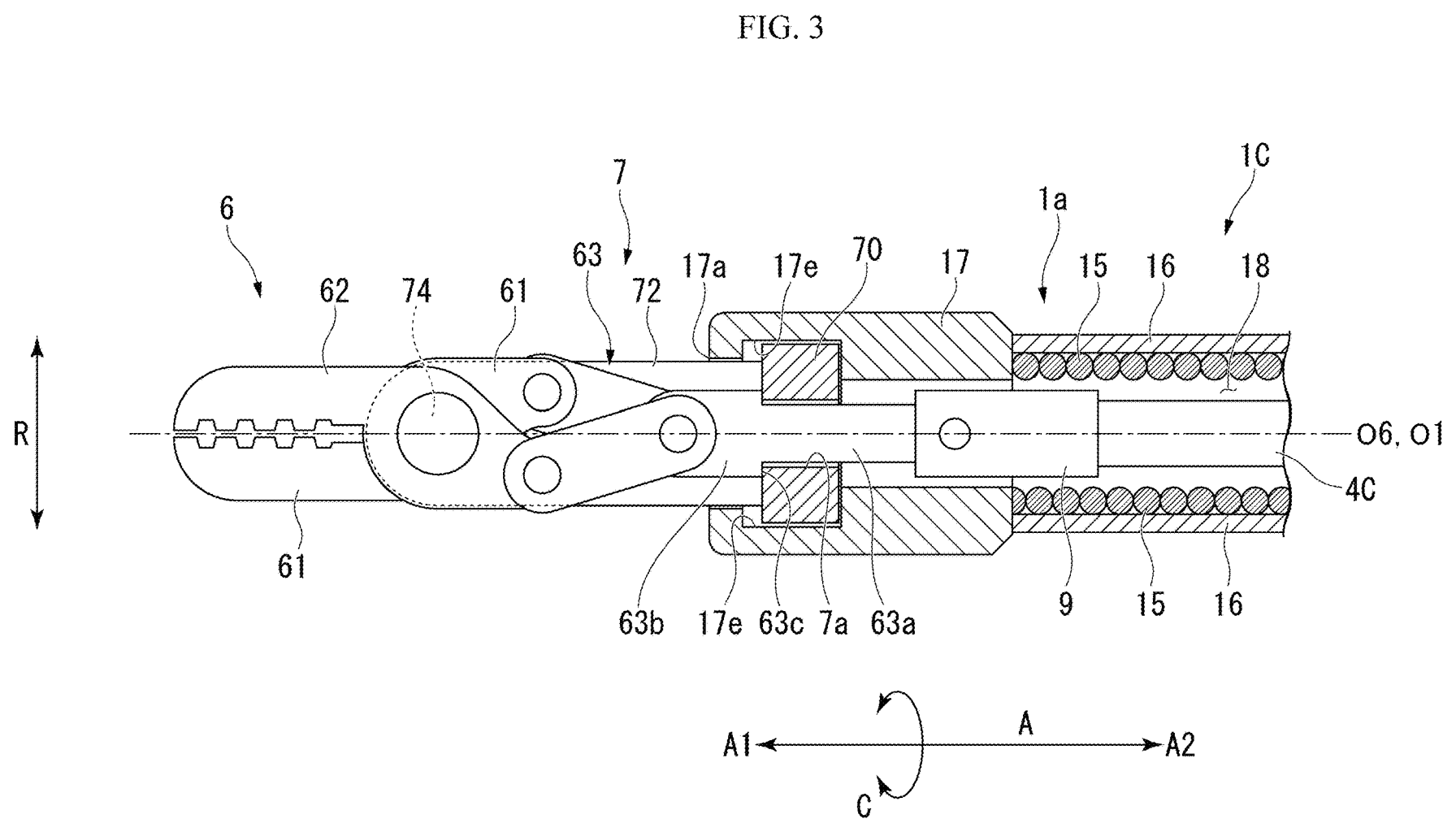

FIG. 3 is a cross-sectional view of a distal end of the treatment device 100C when the forceps 6 are in a closed state.

The sheath 1C includes a coil sheath 15, and a resin sheath 16 in a cylindrical shape that is configured to cover an outer surface of the coil sheath 15. A distal end cover 17 is attached to a distal end 1*a* of the sheath 1C.

The distal end cover 17 is a rigid cylindrical member formed of a metal material or the like. A concave engagement groove 17*e* is formed along a circumferential direction C in the inner circumferential surface of the distal end cover 17.

The sheath 1C includes a water-supply pipeline 18 extending along the longitudinal direction A. The water-supply pipeline 18 communicates with the distal end opening 17*a* formed in the distal end cover 17. The distal end opening 17*a* opens toward the distal end side A1.

Figure 4:
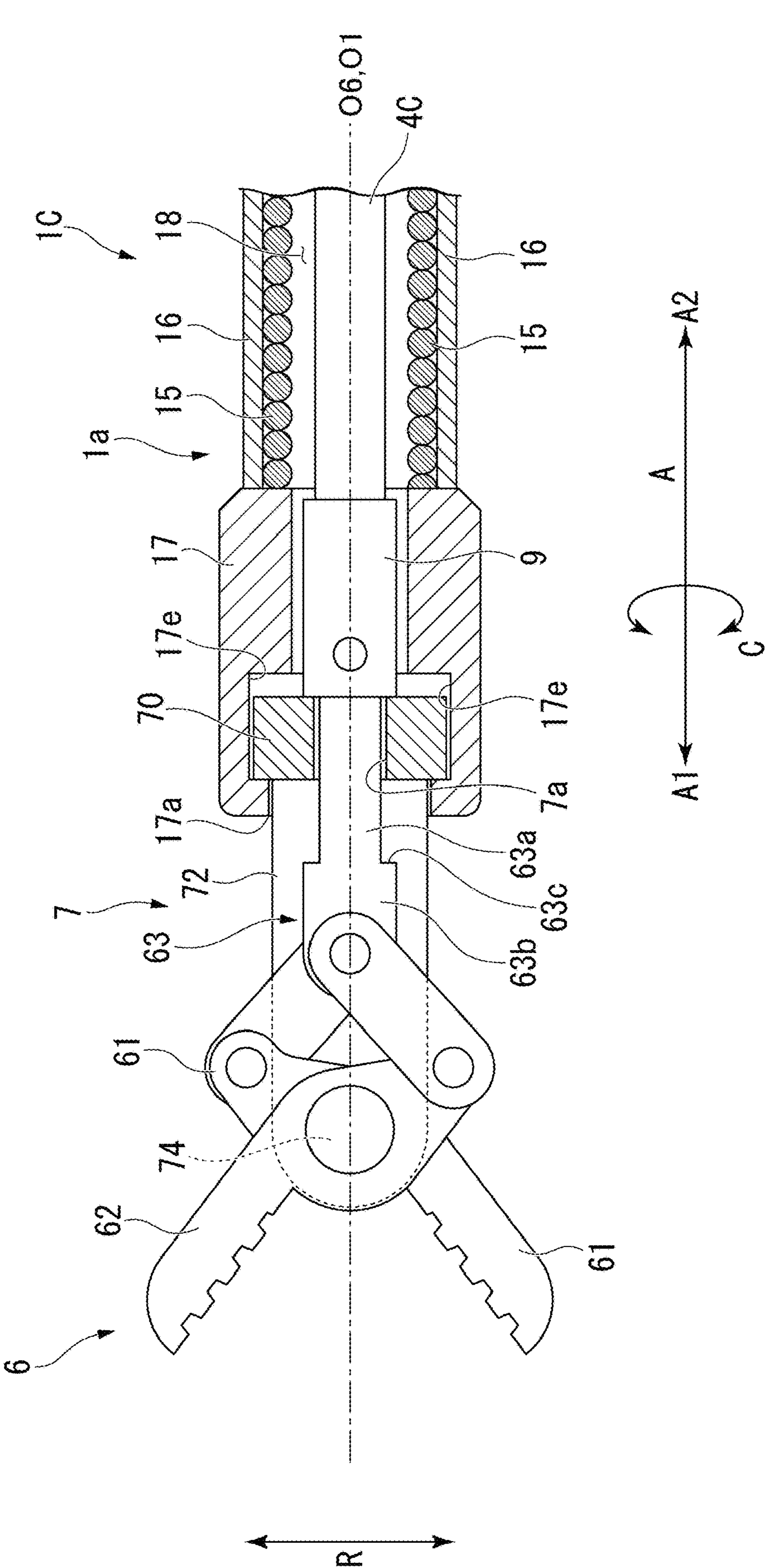
FIG. 4 is a cross-sectional view showing the distal end of the treatment device when the forceps are in an open state.

FIG. 4 is a cross-sectional view of the distal end of the treatment device 100C when the forceps 6 is in an open state.

The forceps (treatment portion) 6 is a grasping forceps that is able to open and close. The forceps 6 has conductivity and is used as the high-frequency knife. The forceps 6 includes a pair of forceps pieces (a first forceps piece 61 and a second forceps piece 62) and a link mechanism 63. The link mechanism 63 and the operation wire 4C configure the operation member for operating the forceps 6.

The pair of forceps pieces (the first forceps piece 61 and the second forceps piece 62) are connected at the link mechanism 63 at the proximal end side A2 and provided to be freely opened and closed toward the distal end side A1. The first forceps piece 61 and the second forceps piece 62 are disposed to be symmetrical with respect to a central axis O6 along the longitudinal direction A of the forceps 6. As shown in FIG. 4, the central axis O6 along the longitudinal direction A of the forceps 6 is substantially coincided with the central axis O1 along the longitudinal direction A of the sheath 1C.

The link mechanism 63 includes a proximal end arm 63*a* at the proximal end side thereof. The proximal end arm 63*a* is formed in a cylindrical shape, for example. The proximal end arm 63*a* is insertable into a central hole 7*a* described below to advance and retract along the longitudinal direction A. The distal end side A1 of the proximal end arm 63*a* includes an enlarged-diameter portion 63*b* whose diameter is enlarged in the radial direction R compared to that of the proximal end arm 63*a*. The enlarged-diameter portion 63*b* includes a contact surface 63*c* that is able to be in contact with the support member 7 at the proximal end side A2.

Figure 5:
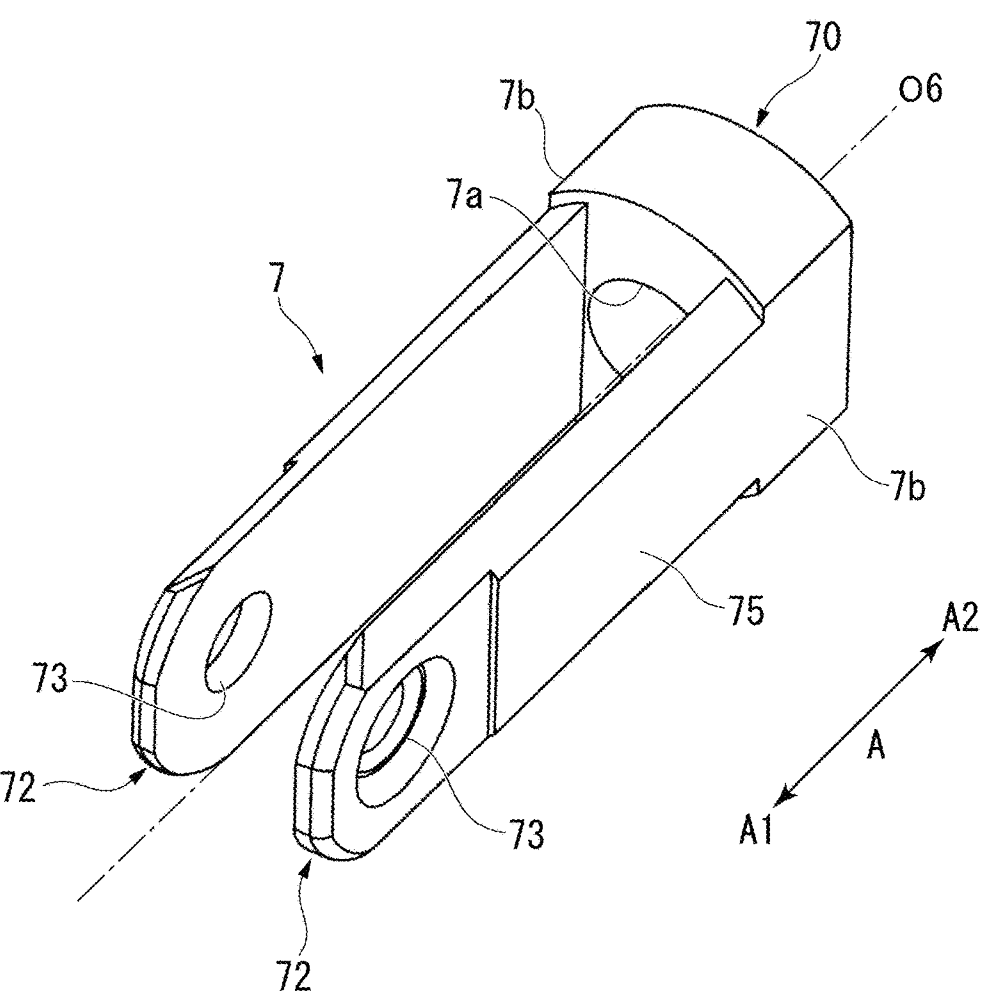
FIG. 5 is a perspective view showing a support member of the treatment device.

FIG. 5 is a perspective view of the support member 7.

The support member 7 is configured to support the forceps 6 so as to be able to open and close the forceps 6 at the distal end 1*a* of the sheath 1C. The support member 7 includes a flow-passage formation member 70 and a bracket 72.

The flow-passage formation member 70 is formed in a disk shape to be engageable with the engagement groove 17*e* of the distal end cover 17, and configured to support the distal end cover 17 to be rotatable around the central axis O1 of the sheath 1C as the rotation center. The flow-passage formation member 70 includes a central hole (first liquid supply hole, penetration hole) 7*a* penetrating along the longitudinal direction A and a notch portion 7*b* provided at the two sides of the central hole 7*a* to sandwich the central hole 7*a* while being concave in the radial direction R. As shown in FIG. 3 and FIG. 4, the proximal end arm 63*a* of the link mechanism 63 is inserted through the central hole 7*a*.

The notch portion 7*b* is formed in a shape by cutting off the outer circumferential surface of the flow-passage formation member 70 at two planes parallel to the axis of the central hole 7*a*. The notch portion 7*b* is disposed at the two sides in a direction orthogonal to the open-close direction of the forceps 6.

The bracket 72 is a pair of plate-shaped members that are disposed at the two sides to sandwich the central axis O6 of the forceps 6. The penetration hole 73 is formed at the distal end side A1 in the bracket 72. As shown in FIG. 3 and FIG. 4, the bracket 72 is configured to support the pair of forceps pieces (the first forceps piece 61 and the second forceps piece 62) via a shaft member 74 penetrating the penetration hole 73 so as to make the pair of forceps pieces rotatable.

The bracket 72 is fixed to the fluid-passage formation member 70 at the proximal end thereof and integrally configured with the fluid-passage formation member 70 to be rotatable around the central axis O1 of the sheath 1C as the rotation center. The bracket 72 and the fluid-passage formation member 70 only have to be integrally rotatable and may be individually configured and then fixed with each other by the welding method, the adhesion method or the like.

As shown in FIG. 5, an outer lateral surface 75 of the bracket 72 is formed on the same plane with the notch portion 7*b* of the fluid-formation member 70.

Figure 6:
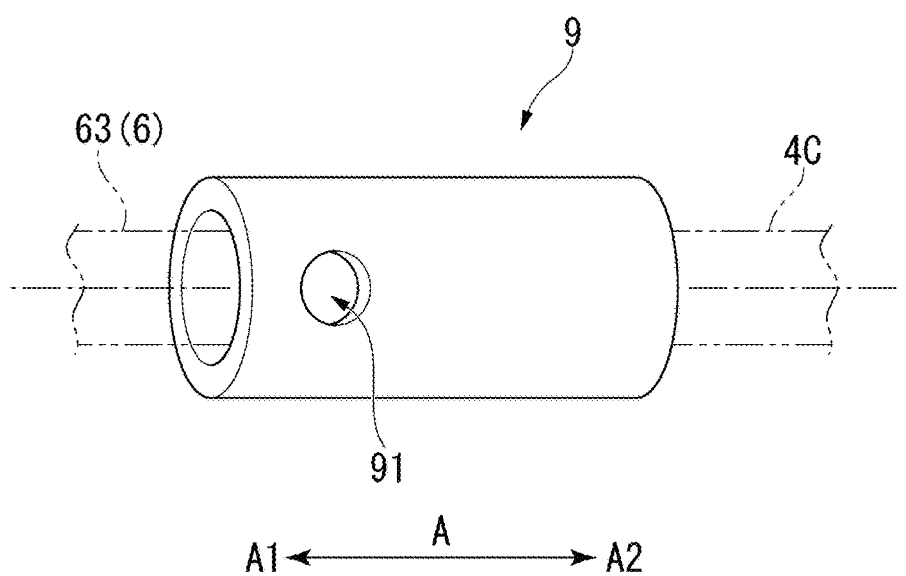
FIG. 6 is a view showing a connection member of the treatment device.

FIG. 6 is a view showing the connection member 9.

The connection member 9 is a cylindrical member configured to connect the distal end of the operation wire 4C and the proximal end arm 63*a* of the link mechanism 63 of the forceps 6. The distal end of the operation wire 4C and the proximal end arm 63*a* of the link mechanism 63 are joined by the brazing method inside the connection member 9. A penetration hole 91 for inserting the wax for the brazing is formed in the connection member 9. The distal end of the operation wire 4C and the proximal end arm 63*a* of the link mechanism 63 may be fixed by the welding method or the adhesion method and the like.

The operation wire 4C is a shaft inserting through the water-supply pipeline 18 of the sheath 1C and has conductivity. The operation wire 4C is formed of a metal material such as the stainless steel or the like. The distal end of the operation wire 4C is connected to the forceps 6 via the connection member 9 and the proximal end of the operation wire 4C is connected to the operation portion 5C.

As shown in FIG. 3, when the operation wire 4C is retracted, the forceps 6 enters the closed state and the contact surface (proximal end surface) 63*c* of the enlarged-diameter portion 63*b* of the link mechanism 63 comes into contact with the distal end of the fluid-passage formation member 70 to block the central hole 7*a* so as to prevent the water from being supplied into the central hole 7*a*. The portion (a second block portion, a second member) for blocking the central hole 7*a* is not limited to the contact surface 63*c* and it only has to be part of the link mechanism 63.

Figure 7:
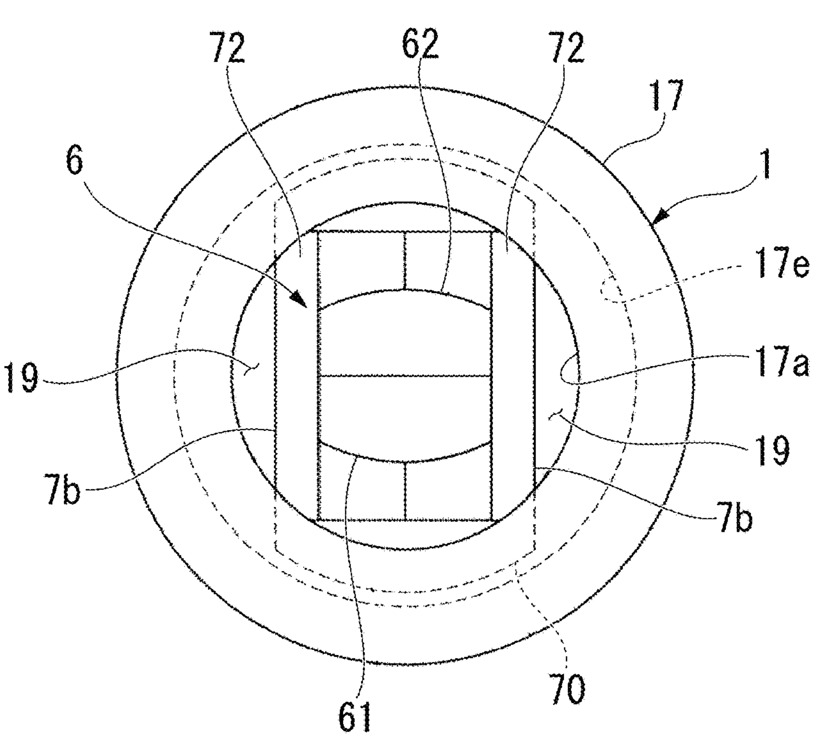
FIG. 7 is a front view showing the distal end of the treatment device when the forceps are in the closed state.

FIG. 7 is a front view showing a distal end of the treatment device 100C when the forceps 6 is in the closed state.

When the forceps 6 enters the closed state to block the central hole 7*a*, the liquid supplied from the water-supply pipeline 18 is supplied to the distal end side A1 only through the second liquid supply hole in a gap between the distal end opening 17*a* of the distal end cover 17 and the notch portion 7*b*. Accordingly, it is possible to prevent the water supply from spreading radially, so as to supply the water almost straightly toward the distal end side.

As shown in FIG. 4, when the operation wire 4C is advanced, the forceps 6 enters the open state and the distal end portion of the connection member 9 comes into contact with the proximal end of the fluid-formation member 70 to block the central hole 7*a* so as to prevent the water from being supplied into the central hole 7*a*. The portion (a first block portion, a first member) for blocking the central hole 7*a* is not limited to the distal end portion of the connection member 9 and it only has to be part of the connection member 9.

Figure 8:
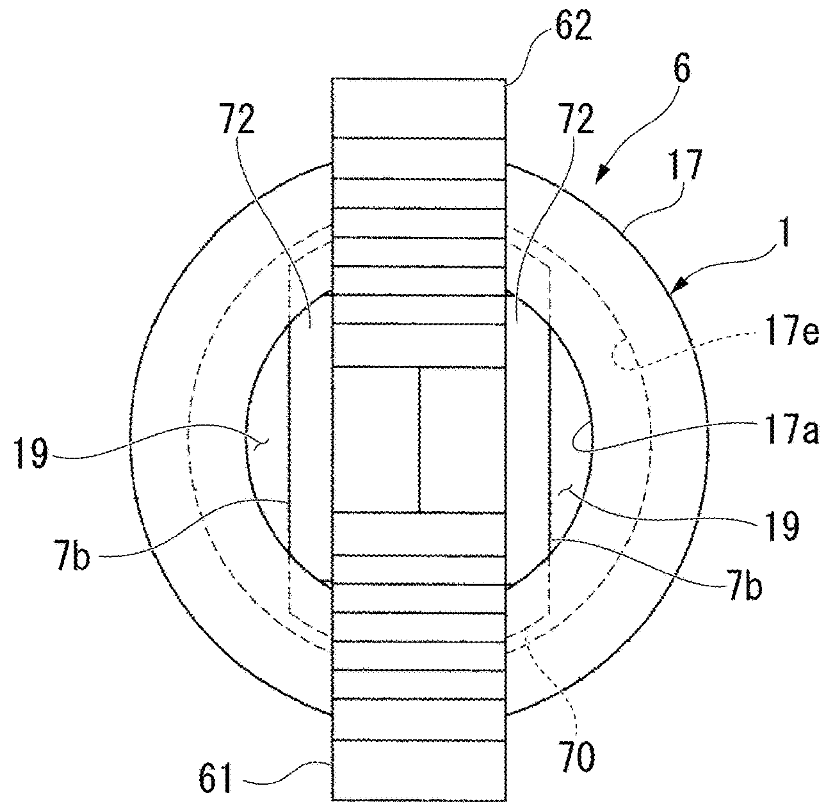
FIG. 8 is a front view showing the distal end of the treatment device when the forceps are in the open state.

FIG. 8 is a front view showing the distal end of the treatment device 100C when the forceps 6 is in the open state.

When the forceps 6 enters the open state to block the central hole 7*a*, the liquid supplied from the water-supply pipeline 18 is supplied to the distal end side A1 only through the second liquid supply hole in a gap between the distal end opening 17*a* of the distal end cover 17 and the notch portion 7*b*. Accordingly, it is possible to prevent the water supply from spreading radially so as to supply the water almost straightly toward the distal end side.

As shown in FIG. 2, the operation portion 5C includes an operation portion main body 51, a slider 52C, a power-supply connection 53C, and a liquid supply port 54C.

The slider 52C is movable along the longitudinal direction A with respect to the operation portion main body 51, and the slider 52C is attached thereto to be rotatable around the axis along the longitudinal direction A as the rotation center. The proximal end 4*b* of the operation wire 4C is attached to the slider 52C. The surgeon advances and retracts the slider 52C with respect to the operation portion main body 51 so as to advance and retract the operation wire 4C. The surgeon rotates the slider 52C around the axis along the longitudinal direction A as the rotation center so as to rotate the operation wire 4C.

The power supply connector 53C is fixed to the operation portion main body 51. The power supply connector 53C is connectable to a high-frequency power supply device which is not shown in figures, and the power supply connector 52C is connected to the proximal end portion of the operation wire 4C. The power supply connector 53C is configured to be able to supply the high-frequency current supplied from the high-frequency power supply device to the forceps 6 via the operation wire 4C.

The liquid supply port 54C is provided in the operation portion main body 51. The liquid supplied from the liquid supply port 54C is drained from the distal end opening 17*a* of the sheath 1C through the water-supply pipeline 18.

[Usage Method of Treatment Device 100C]

Next, the procedures (usage method of the endoscopic treatment system) using the endoscopic system including the treatment device 100C according to the present embodiment will be described. More specifically, the dissection and the peeling procedures, the local injection procedures, and the hemostasis procedures such as the ESD (Endoscopic Submucosal Dissection) procedures or the like with respect to the lesion site during the endoscopic treatment will be described.

As a preparation operation, the surgeon uses the conventional method to specify the lesion site. More specifically, the surgeon inserts the insertion portion 202 of the endoscope 200 into the gastrointestinal tract (such as the esophagus, the stomach, the duodenum, and the large intestine) to specify the lesion site while observing the image captured by the imaging portion 203 of the endoscope.

<Insertion Step>

The surgeon inserts the treatment device 100C into the channel 206 and protrudes the distal end 1*a* of the sheath 1C from the distal end opening portion 206*a* of the insertion portion 202. The surgeon advances the slider 52C of the operation portion 5C with respect to the operation portion main body 51 to protrude the forceps 6.

<Dissection and the Peeling Step>

The surgeon performs the dissection and peeling procedures. The surgeon moves the pair of forceps pieces (first forceps piece 61 and second forceps piece 62) in the closed state while the high-frequency current is energized so as to dissect the mucosa in the lesion site. Then, the surgeon advances the pair of forceps pieces (first forceps piece 61 and second forceps piece 62) in the closed state while the high-frequency current is energized to lift the dissected mucosa in the lesion site to expose the submucosa so as to peel off the submucosa in the dissected lesion site.

As shown in FIG. 3, the pair of forceps pieces (the first forceps piece 61 and second forceps piece 62) are closed such that the central hole 7*a* of the fluid-formation member 70 is blocked by the link mechanism 63.

As shown in FIG. 7, when the pair of forceps pieces (the first forceps piece 61 and second forceps piece 62) are closed, the central hole (first liquid supply hole) 7*a* is blocked by the link mechanism 63. Accordingly, the liquid supplied from the water-supply pipeline 18 is supplied only through the second liquid supply hole 19 in the gap between the distal end cover 17 and the notch portion 7*b* toward the distal end side A1.

Since the central hole (first liquid supply hole) 7*a* is blocked and the area of the cross section of the flow passage for supplying the liquid becomes smaller, the velocity of the supplied liquid increases. The forceps 6 and the bracket 72 at the distal end side A1 of the second liquid supply hole 19 are not obstacles such that the liquid may be supplied straightly toward the distal end side. Accordingly, it is possible to perform the dissection and peeling procedures after removing the bleeding blood.

<Hemostasis Procedures>

In a case in which the bleeding occurs during the dissection and peeling procedures, the surgeon performs the hemostasis procedures. As shown in FIG. 4, the surgeon moves the slider 52C toward the distal end side A1 with respect to the operation portion main body 51 to open the pair of forceps pieces (the first forceps piece 61 and the second forceps piece 62). The surgeon presses the pair of forceps pieces (the first forceps piece 61 and the second forceps piece 62) in the open state to the bleeding point while cauterizing the bleeding point by the energization with the high-frequency current to stop the bleeding (hemostasis step).

As shown in FIG. 4, when the pair of forceps pieces (first forceps piece 61 and second forceps piece 62) are open, the central hole 7*a* of the flow-passage formation member 70 is blocked by the link mechanism 63.

As shown in FIG. 8, when the pair of forceps pieces (first forceps piece 61 and second forceps piece 62) are open, the central hole (first liquid supply hole) 7*a* is blocked by the link mechanism 63. Accordingly, the liquid supplied from the water-supply pipeline 18 is supplied to the distal end side A1 only through the second liquid supply hole 19 in the gap between the distal end cover 17 and the notch portion 7*b*.

The central hole (first liquid supply hole) 7*a* is blocked and the area of the cross section of the flow passage for draining the liquid becomes small such that the velocity of the drained liquid increases. The forceps 6 and the bracket 72 are not obstacles at the distal end side A1 of the second fluid supply hole 19, and thus it is possible to drain the fluid straightly toward the distal end side. Accordingly, it is possible to clearly specify the bleeding point.

In a case in which the mucosa is covered by the liquid such as the blood, the surgeon supplies the liquid through the water-supply pipeline 18 to wash away the bleeding blood and clearly specify the bleeding portion to make it easy to perform the hemostasis procedures.

As shown in FIG. 4, when the pair of forceps pieces (first forceps piece 61 and second forceps piece 62) are open, the central hole (first liquid supply hole) 7*a* of the flow-passage formation member 70 is blocked by the connection member 9.

As shown in FIG. 8, when the pair of forceps pieces (first forceps piece 61 and second forceps piece 62) are open, the central hole (first liquid supply hole) 7*a* is blocked by the connection member 9. Accordingly, the liquid supplied from the water-supply pipeline 18 is supplied to the distal end side A1 only through the second liquid supply hole 19 in the gap between the distal end cover 17 and the notch portion 7*b*.

The central hole 7*a* is blocked and the area of the cross section of the flow passage for draining the liquid becomes small such that the velocity of the drained liquid increases. The forceps 6 and the bracket 72 are not obstacles at the distal end side A1 of the second fluid supply hole 19, and thus it is possible to drain the fluid straightly toward the distal end side. Accordingly, it is possible to definitely wash the target portion.

According to the treatment device 100C disclosed in the present embodiment, it is possible to perform various procedures such as the local injection procedures, the dissection and the peeling procedures, and the hemostasis procedures.

According to the treatment device 100C disclosed in the present embodiment, it is possible to provide the liquid supplied from the water-supply pipeline 18 straightly toward the distal end side from the distal end opening 17*a* when the pair of forceps pieces (first forceps piece 61 and second forceps piece 62) are open or closed.

Hereinbefore, the first embodiment of the present disclosure has been described above; however, the specific configuration thereof is not limited to this embodiment, and modifications within the scope not departing from the spirit of the present disclosure may be included. Also, the configuration may be made by appropriately combining the configurations disclosed in the above-described embodiment and modification examples.

Figure 9:
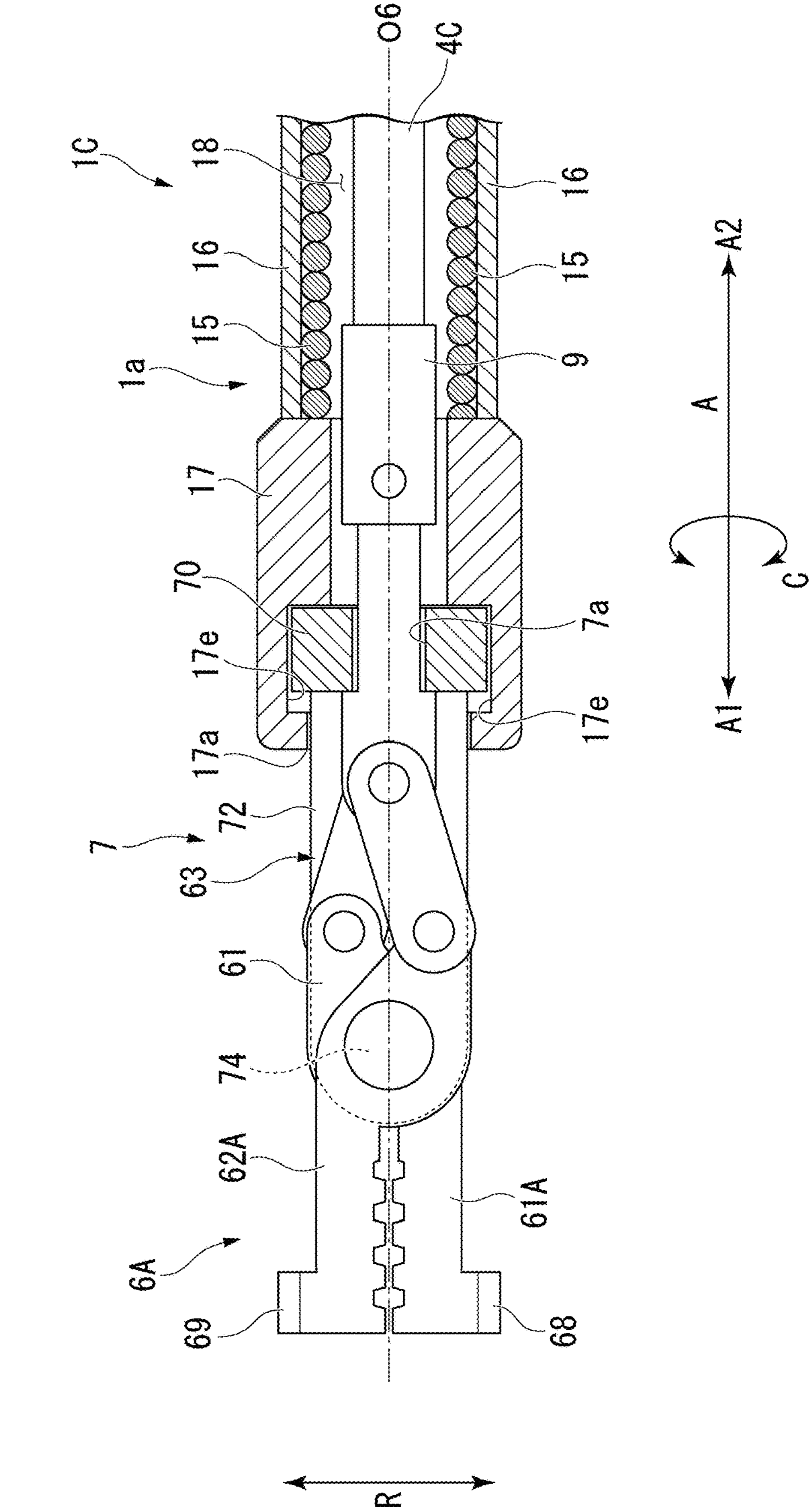
FIG. 9 is a cross-sectional view showing the distal end of the treatment device including a modification example of the forceps.
Figure 10:
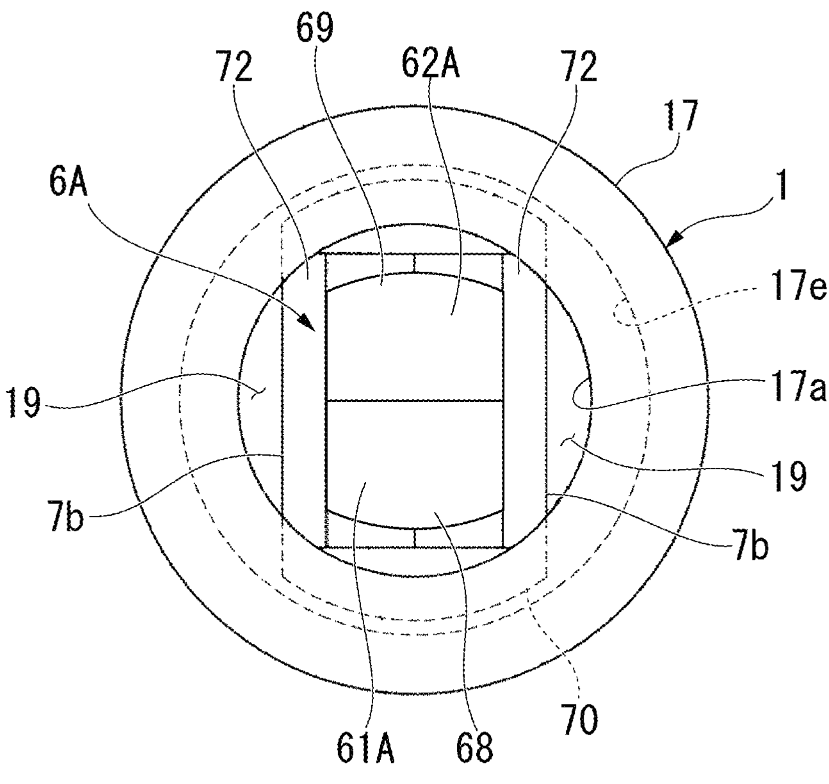
FIG. 10 is a front view showing the distal end of the treatment device including the modification example.

The shape of the forceps 6 is not limited to the shape shown above. FIG. 9 is a cross-sectional view of the treatment device including a forceps 6A as a modification of the forceps 6. FIG. 10 is a front view showing a front view of the treatment device including the forceps 6A. The forceps 6A includes a pair of forceps pieces (first forceps piece 61A and second forceps piece 62A) and the link mechanism 63. The forceps 6A includes a protrusion portion 68 on the upper surface at the distal end of the first forceps piece 61A at the opposite side of the second forceps piece 62A, and a protrusion portion 69 on the lower surface at the distal end of the second forceps piece 62A at the opposite side of the first forceps piece 61A. It is easy for the surgeon to perform the dissection and peeling procedures using the protrusion portion 68 and the protrusion portion 69.

Figure 11:
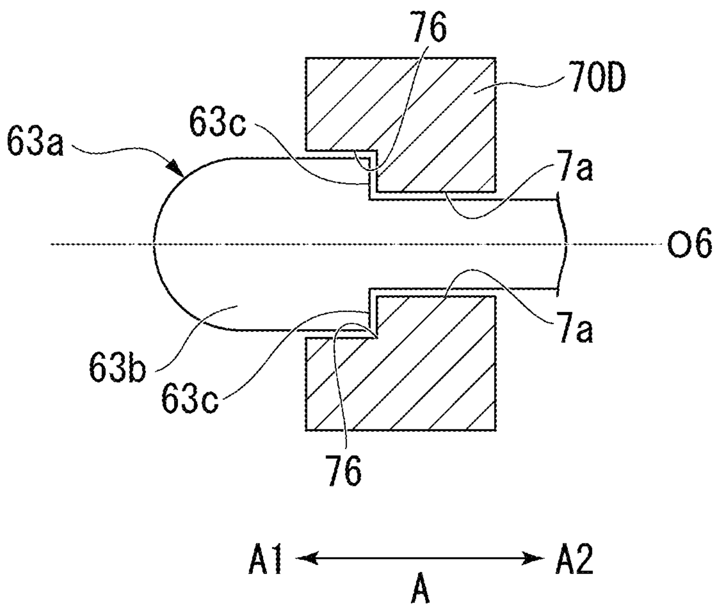
FIG. 11 is a view showing a modification example of a flow-passage formation member of the treatment device.

FIG. 11 is a view showing a flow-passage formation member 70D as a modification example of the flow-passage 70.

The flow-passage formation member 70D includes a concave portion 76 at the distal end side A1 of the central hole 7*a* in which the proximal end side of the enlarged-diameter portion 63*b* is insertable. The portion (second block portion, second member) for blocking the central hole 7*a* is the contact surface 63*c* and the proximal end side of the enlarged-diameter portion 63*b* such that it more suitably blocks the central hole 7*a*.

Figure 12:
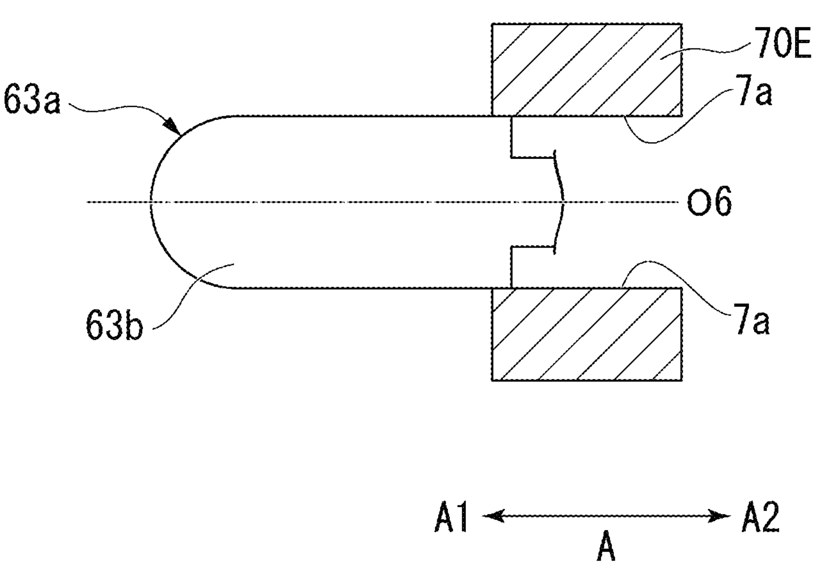
FIG. 12 is a view showing another modification example of the flow-passage formation member of the treatment device.

FIG. 12 is a view showing a flow-passage formation member 70E as a modification of the flow-passage formation member 70.

The central hole 7*a* of the flow-passage formation member 70E is formed such that the proximal end portion of the enlarged-diameter portion 63*b* of the proximal end arm 63*a* can enter, and the enlarged-diameter portion 63*b* entering the central hole 7*a* can engage with the central hole 7*a*. The enlarged-diameter portion 63*b* of the proximal end arm 63*a* entering the central hole 7*a* becomes the portion (second block portion, second member) for blocking the central hole 7*a*. When the operation wire 4C is pulled by the maximum degree, the proximal end portion of the enlarged-diameter portion 63*b* of the proximal end arm 63*a* only comes into contact with the distal end portion in the inner circumferential surface of the central hole 7*a* of the flow-passage formation member 70E so as to more suitably block the central hole 7*a*. At the time of advancing the operation wire 4C, the enlarged-diameter portion 63*b* is separated from the flow-passage formation member 70E.

Figure 13:
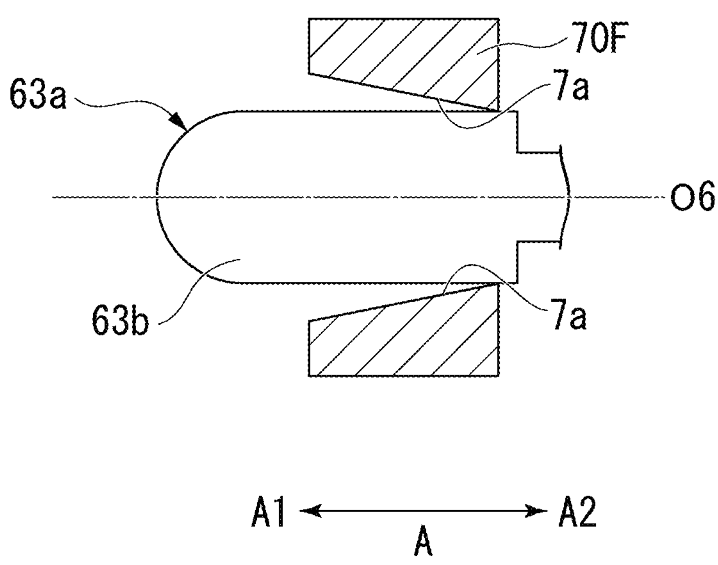
FIG. 13 is a view showing a further modification example of the flow-passage formation member of the treatment device.

FIG. 13 is a view showing a flow-passage formation member 70F as a modification example of the flow-passage member 70.

The inner circumferential surface of the central hole 7*a* of the flow-passage formation member 70F is formed in a tapered shape that broadens at the distal end side A1. The enlarged-diameter portion 63*b* of the proximal end arm 63*a* is configured to further suitably block the central hole 7*a* by only coming into contact with the proximal end portion in the inner circumferential surface of the central hole 7*a* of the flow-passage formation member 70F.

Figure 14:
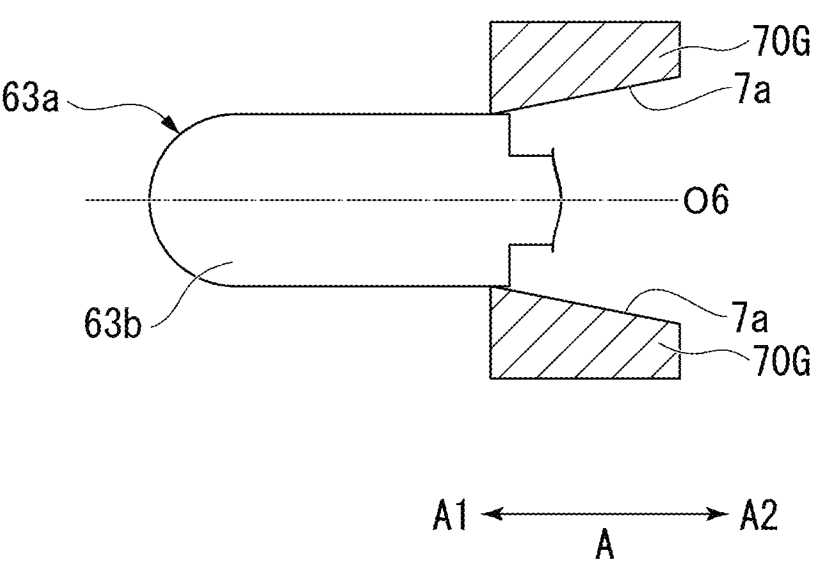
FIG. 14 is a view showing a further modification example of the flow-passage formation member of the treatment device.

FIG. 14 is a view showing a flow-passage formation member 70G as a modification example of the flow-passage formation member 70.

The inner circumferential surface of the central hole 7*a* of the flow-passage formation member 70G is formed in a tapered shape that broadens at the proximal end side A2. When the operation wire 4C is pulled to the maximum degree, the proximal end portion of the enlarged-diameter portion 63*b* of the proximal end arm 63*a* only comes into contact with the distal end portion in the inner circumferential surface of the central hole 7*a* of the flow-passage formation member 70G so as to more suitably block the central hole 7*a*. At the time of advancing the operation wire 4C, the enlarged-diameter portion 63*b* is separated from the flow-passage formation member 70G.

Figure 15:
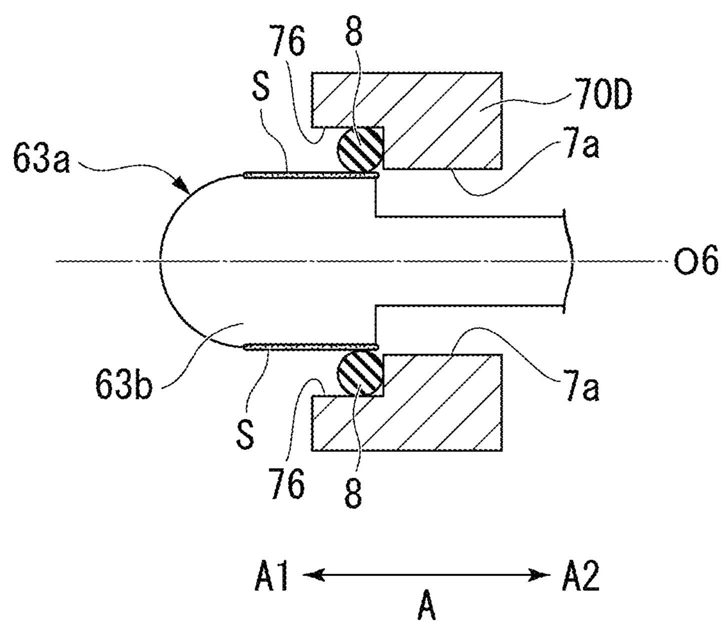
FIG. 15 is a view showing the flow-passage formation member further including an O-ring.

FIG. 15 is a view showing the flow-passage formation member 70D further including an O-ring 8. The O-ring 8 is provided in the concave portion 76 and the O-ring 8 is able to fit with the enlarged-diameter portion 63*b* of the proximal end arm 63*a*. The enlarged-diameter portion 63*b* of the proximal end arm 63*a* is configured to fit with the O-ring 8 so as to more suitably block the central hole 7*a*. It is preferable to apply the silicone oil S on the portion fitting with the O-ring 8 in advance.

Figure 16:
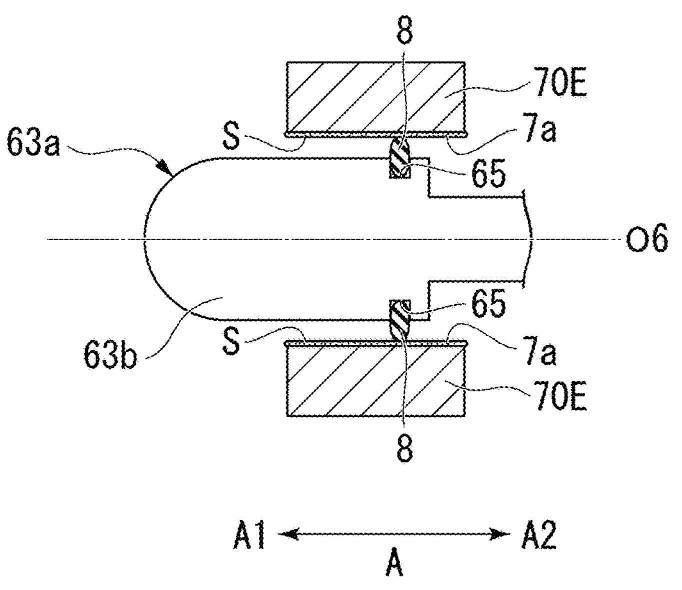
FIG. 16 is a view showing a proximal end arm further including an O-ring.

FIG. 16 is a view showing the proximal end arm 63*a* further including the O-ring 8.

The O-ring 8 is fitted into the concave portion 65 formed in the outer circumferential portion of the enlarged-diameter portion 63*b*. The enlarged-diameter portion 63*b* of the proximal end arm 63*a* is configured to more suitably block the central hole 7*a* since the O-ring 8 fitted with the concave portion 65 is fitted with the central hole 7*a*. It is preferable to apply the silicone oil S on the portion fitting with the O-ring 8 in advance.

Figure 17:
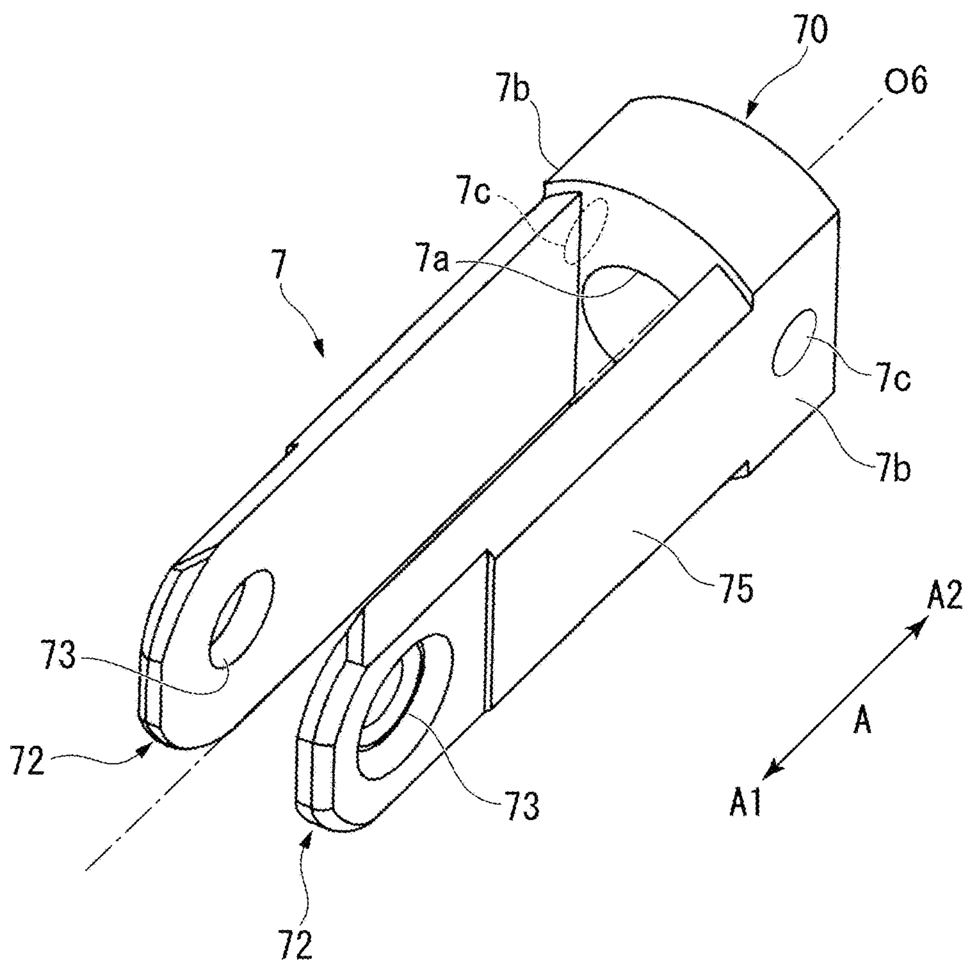
FIG. 17 is a perspective view showing another modification example of the flow-passage formation member.

FIG. 17 is a perspective view showing a flow-passage formation member 70H as a modification example of the flow-passage formation member 70.

The flow-passage formation member 70H further includes a lateral hole 7*c* in the notch portion 7*b* that communicates with the central hole 7*a*. The lateral hole 7*c* is disposed at two sides of the central hole 7*a* to sandwich the axis of the central hole 7*a*. When the operation wire 4C is retracted, the forceps 6 enters the closed state while the contact surface (proximal end surface) 63*c* of the enlarged-diameter portion 63*b* of the link mechanism 63 comes into contact with the distal end of the flow-passage formation member 70H such that the distal end side A1 of the central hole 7*a* is blocked. When the distal end side A1 of the central hole 7*a* is blocked, the fluid passing through the central hole 7*a* cannot flow toward the distal end side A1 from the central hole 7*a*; however, the fluid can flow toward the second fluid supply hole 19 via the lateral hole 7*c*. Accordingly, when the distal end side A1 of the central hole 7*a* is blocked, it is possible to increase the flow rate of the fluid passing through the second fluid supply hole 19.

Although the respective embodiments and modifications of the present disclosure have been described above, the technical scope of the present disclosure is not limited to the above-described embodiments, and includes configurations in the respective embodiments and modifications within the scope of the claims not departing from the spirit of the present disclosure. It is possible to change the combination of elements, make various changes to each configuration element, or delete each configuration element. For example, the configuration according to any one of above-described embodiments and modifications of the present disclosure may be appropriately combined with each modification of the operation section. The present disclosure is not limited by the above description, but only by the appended claims.

What is claimed is:

1. An endoscopic treatment device comprising:
- a sheath including a lumen;
- a passage member provided at a distal end of the sheath and having a penetration hole extending along a longitudinal axis of the sheath;
- a treatment portion that is configured to cauterize tissue and is conductive;
- an elongated member configured to provide current to the treatment portion and extend in the lumen;
- a first block portion configured to abut against a proximal end of the passage member when advancing the elongated member; and
- a second block portion configured to abut against a distal end of the passage member when retracting the elongated member.

2. The endoscopic treatment device according to claim 1, wherein:
- the penetration hole is in fluid communication with the lumen, and
- the lumen is configured to provide fluid to the penetration hole.

3. The endoscopic treatment device according to claim 1, wherein:
- the first block portion and the second block portion have a cross-sectional width that is larger than a cross-sectional width of a proximal portion of the treatment portion, and
- the proximal portion of the treatment portion is passed through the penetration hole of the passage member.

4. The endoscopic treatment device according to claim 1, wherein:
- a distal end of the treatment portion is enlarged relative to a proximal portion of the treatment portion, and
- the proximal portion of the treatment portion is passed through the penetration hole of the passage member.

5. The endoscopic treatment device according to claim 1, wherein:
- at least one of the first block portion and the second block portion has a cross-sectional width that is larger than a cross-sectional width of a proximal portion of the treatment portion and less than a cross-sectional width of a distal end of the treatment portion, and
- the proximal portion of the treatment portion is passed through the penetration hole of the passage member.

6. The endoscopic treatment device according to claim 1, wherein the first block portion is configured to block a proximal end of the penetration hole by coming into contact with a proximal end surface of the passage member.

7. The endoscopic treatment device according to claim 1, wherein the second block portion is configured to block a distal end of the penetration hole by coming into contact with a distal end surface of the passage member.

8. The endoscopic treatment device according to claim 1, further comprising:
- an operation member connected to the treatment portion, wherein the operation member includes a link mechanism connected to the treatment portion and an operation wire extending along the longitudinal axis of the sheath.

9. The endoscopic treatment device according to claim 8, further comprising:
- a connector configured to connect a proximal end arm of the link mechanism and the operation wire, wherein the connector includes the first block portion.

10. The endoscopic treatment device according to claim 9, wherein the passage member includes a notch portion configured to form a second liquid supply hole as a gap between a distal end cover of the sheath and the notch portion.

11. The endoscopic treatment device according to claim 10, wherein a lateral hole communicating with the penetration hole is formed in the notch portion.

12. The endoscopic treatment device according to claim 9, wherein the link mechanism includes the second block portion.

13. The endoscopic treatment device according to claim 9, wherein the proximal end arm is inserted into the penetration hole of the passage member.

14. The endoscopic treatment device according to claim 1, wherein the passage member includes a notch portion configured to form a second liquid supply hole as a gap between a distal end cover of the sheath and the notch portion.

15. The endoscopic treatment device according to claim 1, wherein an outer diameter of the first block portion and an outer diameter of the second block portion each are larger than a diameter of the penetration hole and smaller than an inner diameter of the sheath.

16. The endoscopic treatment device according to claim 9, wherein:

the treatment portion comprises a pair of forceps, when the pair of forceps are closed, the proximal end arm of the link mechanism comes into contact with the passage member, and when the pair of forceps are opened, a distal end portion of the connector comes into contact with the passage member.

17. The endoscopic treatment device according to claim 9, wherein:

the treatment portion comprises a pair of forceps, when the proximal end arm of the link mechanism is retracted in a direction along the longitudinal axis of the sheath, the proximal end arm comes into contact with the passage member and the pair of forceps are closed, and when the connector is advanced in the direction along the longitudinal axis of the sheath, a distal end portion of the connector comes into contact with the passage member and the pair of forceps are opened.

18. An endoscopic treatment device comprising:

a sheath including a lumen;

a passage member attached to a distal end portion of the sheath;

a treatment portion configured to deliver energy to a treatment site;

an elongated member that is configured to provide current to the treatment portion and extend in the lumen;

a first block portion configured to come into contact with a proximal end of the passage member when advancing the elongated member; and a second block portion configured to come into contact with a distal end of the passage member when retracting the elongated member.

19. The endoscopic treatment device according to claim 18, further comprising:

an operation member connected to the treatment portion, wherein:

the operation member includes a link mechanism connected to the treatment portion and an operation wire extending along a longitudinal axis of the sheath, the treatment portion comprises a pair of forceps pieces that are configured to open and close, and when the pair of forceps pieces are closed, a proximal end arm of the link mechanism comes into contact with the passage member.

20. The endoscopic treatment device according to claim 18, further comprising:

an operation member connected to the treatment portion, the operation member including:

a link mechanism connected to the treatment portion; and an operation wire extending along a longitudinal axis of the sheath; and a connector configured to connect a proximal end arm of the link mechanism and the operation wire, wherein the connector includes the first block portion, wherein:

the treatment portion comprises a pair of forceps pieces that are configured to open and close, and when the pair of forceps pieces are opened, a distal end portion of the connector comes into contact with the passage member.

21. An endoscopic treatment device comprising:

a sheath including a lumen;

a passage member provided at a distal end of the sheath and having a penetration hole extending along a longitudinal axis of the lumen;

a treatment portion comprising an electrically conductive material;

an operation member that is extended in the lumen and configured to move along the longitudinal axis of the lumen; and a first block portion and a second block portion, wherein:

the first block portion and the second block portion have a cross-sectional width that is larger than a cross-sectional width of a proximal portion of the treatment portion, the proximal portion of the treatment portion is passed through the penetration hole of the passage member, and the penetration hole is in fluid communication with the lumen when the first block portion or second first block portion does not contact the passage member.

* * * * *